United States Patent [19]

Campbell et al.

[11] Patent Number: 5,758,664
[45] Date of Patent: Jun. 2, 1998

[54] METHOD OF MAINTAINING A LEFT VENTRICULAR ASSIST DEVICE

[75] Inventors: Michael L. Campbell; John R. Daugherty; Edward E. Shaw; Pete L. Villalpando, all of Flagstaff, Ariz.

[73] Assignee: W. L. Gore & Associates, Inc., Newark, Del.

[21] Appl. No.: 663,003

[22] Filed: Jun. 6, 1996

Related U.S. Application Data

[63] Continuation-in-part of Ser. No. 484,254, Jun. 7, 1995, Pat. No. 5,647,380.
[51] Int. Cl.$^6$ ...................................................... A61B 19/00
[52] U.S. Cl. ................................................ 128/898; 600/16
[58] Field of Search .......................... 600/16, 17; 128/898; 623/3

[56] References Cited

U.S. PATENT DOCUMENTS

| | | |
|---|---|---|
| 3,953,566 | 4/1976 | Gore . |
| 4,187,390 | 2/1980 | Gore . |
| 4,813,952 | 3/1989 | Khalafalla . |
| 4,919,661 | 4/1990 | Gibney . |
| 4,968,293 | 11/1990 | Nelson . |
| 4,979,936 | 12/1990 | Stephenson et al. . |
| 4,995,857 | 2/1991 | Arnold . |
| 5,007,927 | 4/1991 | Bedylak et al. . |
| 5,192,314 | 3/1993 | Daskalakis . |
| 5,332,403 | 7/1994 | Kolff . |
| 5,534,023 | 7/1996 | Henley . |
| 5,571,176 | 11/1996 | Taheri . |
| 5,647,380 | 7/1997 | Campbell et al. ................ 128/898 |

OTHER PUBLICATIONS

Clark M, Springen K. Help for the Heart: Back Muscle. Newsweek Dec. 22, 1986;57.
Macoviak, JA et al. Replacement of ventricular myocardium with diaphragmatic skeletal muscle. J Thorac Cardiovasc Surg 1981; 91:519–527.
Mannion JD et al. Hydraulic pouches of canine latissimus dorsi. J Thorac Cardiovasc Surg 1986; 91:534–544.

Niinami H et al. A New Configuration for Right Ventricular Assist With Skeletal Muscle Ventricle. Circulation 1991;84:2470–2475.

Thomas GA et al. Pericardium–Lined Skeletal Muscle Ventricles in Circulation up to 589 Days. Ann Thorac Surg 1994; 58:978–88.

Ruggiero et al "Skeletal Muscle Ventricles: Update After 18 Months in Circulation." Artificial Organs 15(5):350–354, Oct. 1991.

*Primary Examiner*—Vincent Millin
*Assistant Examiner*—Kelly O'Hara
*Attorney, Agent, or Firm*—Wayne D. House

[57] ABSTRACT

A method of making a left ventricular assist device (LVAD) using muscle wrapped around a mandrel to form a muscle pouch, the open end of which is sewn to a circular sheet of patch material having connections to one end of each of a pair of vascular grafts, or alternatively to one end of a single vascular graft. The second ends of these vascular grafts are used to connect the LVAD to the aorta. After the muscle pouch has been formed around the mandrel, the mandrel is removed and replaced by a balloon which is inserted into the muscle pouch and inflated to maintain the desired shape of the muscle pouch during healing and stimulation of the pouch. The balloon is subsequently removed preceding activation of the LVAD to allow it to begin pumping blood. Alternatively, various other shape-maintaining forms which are expandable and collapsible may be used in place of the balloon. In an alternative embodiment, an additional strip of latissimus dorsi or other appropriate muscle or a mechanical clamping device may be used to synchronously compress the aorta between the ends of the vascular grafts anastomosed to the aorta.

18 Claims, 19 Drawing Sheets

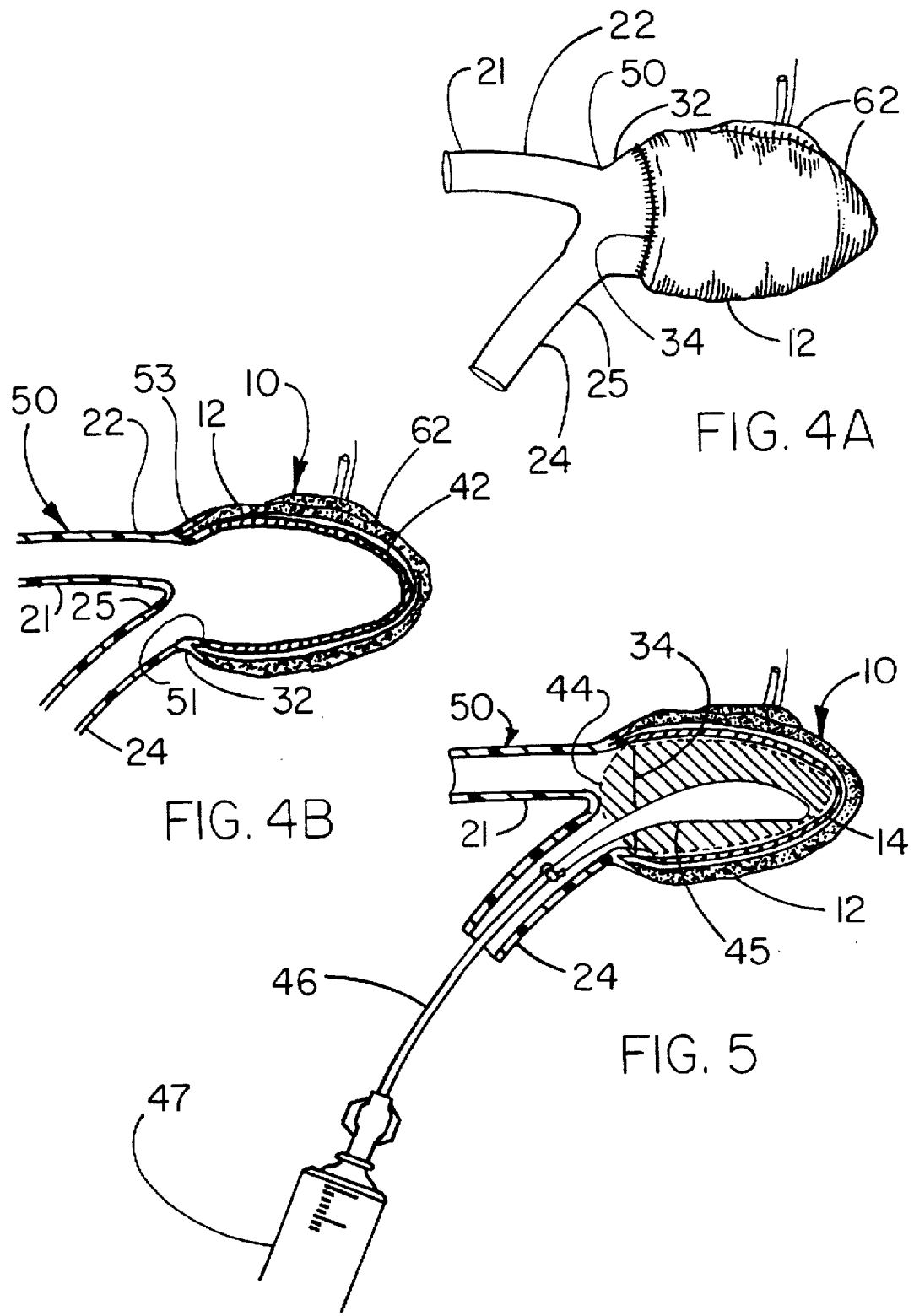

METHOD OF MAINTAINING A LEFT VENTRICULAR ASSIST DEVICE

CROSS REFERENCE TO RELATED APPLICATIONS

This application is a continuation-in-part of application Ser. No. 08/484,254 filed Jun. 7, 1995, now U.S. Pat. No. 5,647,380.

FIELD OF INVENTION

This invention relates to the field of left ventricular assist devices.

BACKGROUND OF THE INVENTION

Left Ventricular Assist Devices (LVADs) are auxiliary pouches intended to function as booster pumps to aid the hearts of individuals suffering from chronic congestive heart failure. This condition is frequently due to heart attacks that reduce the pumping capacity of the human heart. By boosting the capacity of such a weakened heart, individuals suffering from this condition may be allowed to again lead relatively normal, effective lives.

While various designs of LVADs have been proposed, the most promising appears to be an auxiliary pouch formed from the individual's latissimus dorsi muscle and controlled by a pacemaker. This approach avoids potential rejection problems related to the use of other non-autologous materials and takes advantage of well-developed pacemaker and prosthetic vascular graft technology. LVADs of this type are commonly called skeletal muscle ventricles (SMVs). Much of the developmental work on these devices has been accomplished by Dr. Larry Stephenson and colleagues at Wayne State University. Their work has been described in various articles in the literature; see, for example, 1) Clark M, Springen K, Help For The Heart: Back Muscle. Newsweek Dec. 22, 1986. 2) Mannion J D et al., Hydraulic pouches of canine latissimus dorsi: Potential for left ventricular assistance. Journal of Thoracic Cardiovascular Surgery 1986; 91: 534–544. 3) U.S. Pat. No. 4,979,936. 4) Thomas G A et al. Pericardium-Lined Skeletal Muscle Ventricles in Circulation up to 589 Days. Society of Thoracic Surgeons 1994; 58: 1–11.

Based on development work done previously on beagles, it is anticipated that the procedure for creating such an SMV in a human would involve making an incision to expose the left latissimus dorsi muscle and dissecting the muscle free from the subcutaneous tissues and chest wall, except for the neurovascular bundle and humeral insertion. A bipolar nerve cuff electrode is placed around the thoracodorsal nerve. The nerve lead is connected to an inactive neurostimulator, buried beneath the left rectus abdominis muscle, which innervates the exposed latissimus dorsi muscle.

Next, the left chest is opened at the fourth rib. Preferably, the fourth rib is removed to provide more space for the LVAD. Optionally, the anterior pericardium is removed between the phrenic nerves and used to cover a conically-shaped mandrel of biocompatible plastic. Mandrels used for beagles had a diameter of about 3 cm, length of about 6.5 cm and volume of about 25 ml; a mandrel suitable for forming a human SMV would need to be appropriately enlarged. After wrapping the pericardium around the mandrel it is sewn to a 5 mm thick collar of synthetic material such as woven Dacron felt placed at the base of the mandrel. The dorsal edge of the latissimus dorsi muscle is then folded longitudinally upon itself and secured by sutures, after which the medial aspect of the latissimus dorsi muscle is wrapped around the mandrel (and over the pericardium if it was used) about 2–2.5 times with the folded edge of the muscle sewn circumferentially to the Dacron felt collar. The SMV is then positioned subcutaneously and the wound is closed and allowed to heal for three weeks.

Following this healing period, the neurostimulator is activated to deliver continuously a 2 Hz stimulation of 210 microsecond duration and 1 to 2 volt amplitude. The purpose of the stimulation is to transform the fatigable Type II latissimus dorsi muscle fibers to fatigue-resistant Type I muscle fibers. Typically, 6 weeks are allowed for this stimulation period, after which the chest is again opened to connect the formed muscle pouch to the aorta. This is accomplished by first attaching sensing leads to the left ventricle. The descending thoracic aorta is exposed to allow two 12 mm ringed vascular grafts to be anastomosed to the aorta, one above the other, in end-to-side fashion.

After completion of these anastomoses, a cotton tape is passed around the aorta between the two graft anastomoses for subsequent ligation of the aorta. Next, a circular 3.5 cm diameter piece of patch material is cut from a sheet of 0.6 mm thick GORE-TEX® Cardiovascular Patch. This circular piece may optionally be formed into a concave, cup-like shape. A pair of 12 mm diameter holes are cut through this sheet to accommodate anastomosis of the opposite ends of the two vascular grafts. The plastic mandrel is removed from within the muscle pouch. The Dacron felt collar remains. The 3.5 cm diameter circular piece of GORE-TEX Cardiovascular Patch is sewn over the open end of the muscle pouch (with the concave side facing the pouch if the patch was so formed) and the opposite ends of the two vascular grafts are anastomosed to the 12 mm diameter holes in the patch. The aorta is then at least partially ligated forcing blood flow through the newly formed SMV. Finally, the nerve lead and myocardial leads are connected to an R-wave synchronous pulse-train stimulator.

Alternatively, the vascular grafts may be provided with valves (such as prosthetic heart valves) to control the flow of blood through the LVAD. The use of valves may obviate the need to ligate the aorta.

SMVs made as described above have been demonstrated to generate significant increases in cardiac output in Beagle dogs for periods of longer than 19 months. While effectiveness in humans remains to be demonstrated, animal results thus far appear promising.

A fundamental disadvantage of the above procedure lies in the removal of the plastic mandrel from the muscle pouch, sewing the patch material to the pouch and anastomosis of the vascular grafts to the patch material immediately preceding activation of the SMV. The needle punctures immediately preceding exposure of the SMV and vascular grafts to blood pressure often result in suture line bleeding at the patch and vascular graft suture lines and may result in disruption of a suture line.

SUMMARY OF THE INVENTION

The present invention relates to a revised LVAD procedure wherein after forming the SMV around the plastic mandrel, the mandrel is replaced by an inflatable balloon of biocompatible material which, after inflation, is used to maintain the shape of the SMV during healing and stimulation period during which the SMV is converted from the fatiguable Type II muscle fibers to fatigue-resistant Type I muscle fibers. The use of a balloon allows for an increased amount of the construction of the LVAD to be performed during the initial surgery. According to one embodiment, virtually the entire LVAD can be constructed during the first surgery. In addition to allowing for more complete healing of the LVAD before it is used for pumping blood, the stimulation period is anticipated to be more effective because the SMV is working dynamically against an inflated balloon rather than isometrically against a rigid mandrel.

According to the method of the present invention, the muscle pouch is formed and sewn around the plastic mandrel. The mandrel is then removed and the muscle pouch is sewn to a circular piece of patch material that incorporates one or two vascular grafts previously anastomosed to the circular piece of patch material in a leak-proof fashion. The inflatable balloon is then introduced into the muscle pouch via one of the vascular grafts and inflated by a small conduit for the balloon extending through the vascular graft and connecting to the balloon within the muscle pouch. Again via the small conduit, the balloon can be deflated after the three week healing period and six week stimulation is period, and removed from within the muscle pouch via the end of the vascular graft opposite the muscle pouch. In addition to allowing for nine weeks of healing of the seam line between the circular patch and muscle pouch, the inventive process also simplifies the second surgery in that essentially only removal of the balloon, anastomosis of the grafts, ligation of the aorta and connection of the nerve and myocardial leads to the stimulator are required prior to activation of the SMV.

In an alternative embodiment, the anastomoses of the one or two vascular grafts to the aorta are performed during the first surgery. The vascular graft or grafts are maintained in an occluded state during the healing and stimulation period by the use of balloons. The vascular graft occlusion balloon or balloons are deflated and removed following this period along with the balloon used to maintain the shape of the SMV during the healing and stimulation period, for example, from a small opening in the end of the SMV opposite the end sewn to the circular patch material. This may be accomplished through a small subcutaneous incision to provide the necessary access; the small opening in the end of the SMV is then closed prior to activation of the LVAD. Alternatively the balloon may be removed through one of the vascular grafts. Such methods eliminate the need to perform a second major surgery in order to anastomose the vascular graft or grafts to the aorta.

While latissimus dorsi muscle is conventionally used to form the muscle pouch (optionally over a layer of pericardium), it is believed that it may be possible to use other Type II muscles as well.

Further, the circular patch material sewn to the base of the muscle pouch may be provided with two or three flanges around the circumference of the patch if it is desired to use pericardium, a covering layer of synthetic material such as GORE-TEX® Preclude Pericardial Membrane, or both in addition to the latissimus dorsi muscle. The use of such a synthetic material may be desirable to help prevent adhesion of surrounding tissue to the exterior of the SMV. By providing the circular patch material with two or more circumferential flanges, the various individual layers forming the SMV may be sewn to the patch between the adjacent circumferential flanges of the patch.

In another embodiment, intermittent ligation of the aorta may be accomplished by the use of a separate strip of latissimus dorsi muscle wherein the end of the strip wraps around the aorta in place of the conventional ligation. This end of the latissimus dorsi muscle strip can then compress the aorta to cause closure of the aortic passageway between the vascular grafts. This can be done cyclically with activation of the SMV so that the aorta will be closed by the latissimus dorsi muscle strip only during systolic action of the SMV. In the event of functional failure of the SMV, the strip of latissimus dorsi muscle would be relaxed by deactivating the neurostimulator. Alternatively, a mechanical clamping device may be used to effect ligation of the aorta, either cyclically or continuously, during use of the SMV and deactivated to release clamping of the aorta in the event of failure of the SMV. Sensing systems to actuate such a mechanical clamp are known in the fields of pacemakers and defibrillators.

BRIEF DESCRIPTION OF THE DRAWINGS

FIGS. 4A and 4B describe the completed SMV after attachment of the vascular graft and circular patch assembly.

FIG. 5 describes insertion and inflation of a balloon intended to maintain the desired shape of the SMV during healing and stimulation of the latissimus dorsi muscle to convert it from Type II to Type I muscle.

DETAILED DESCRIPTION OF THE INVENTION

Figure 1:
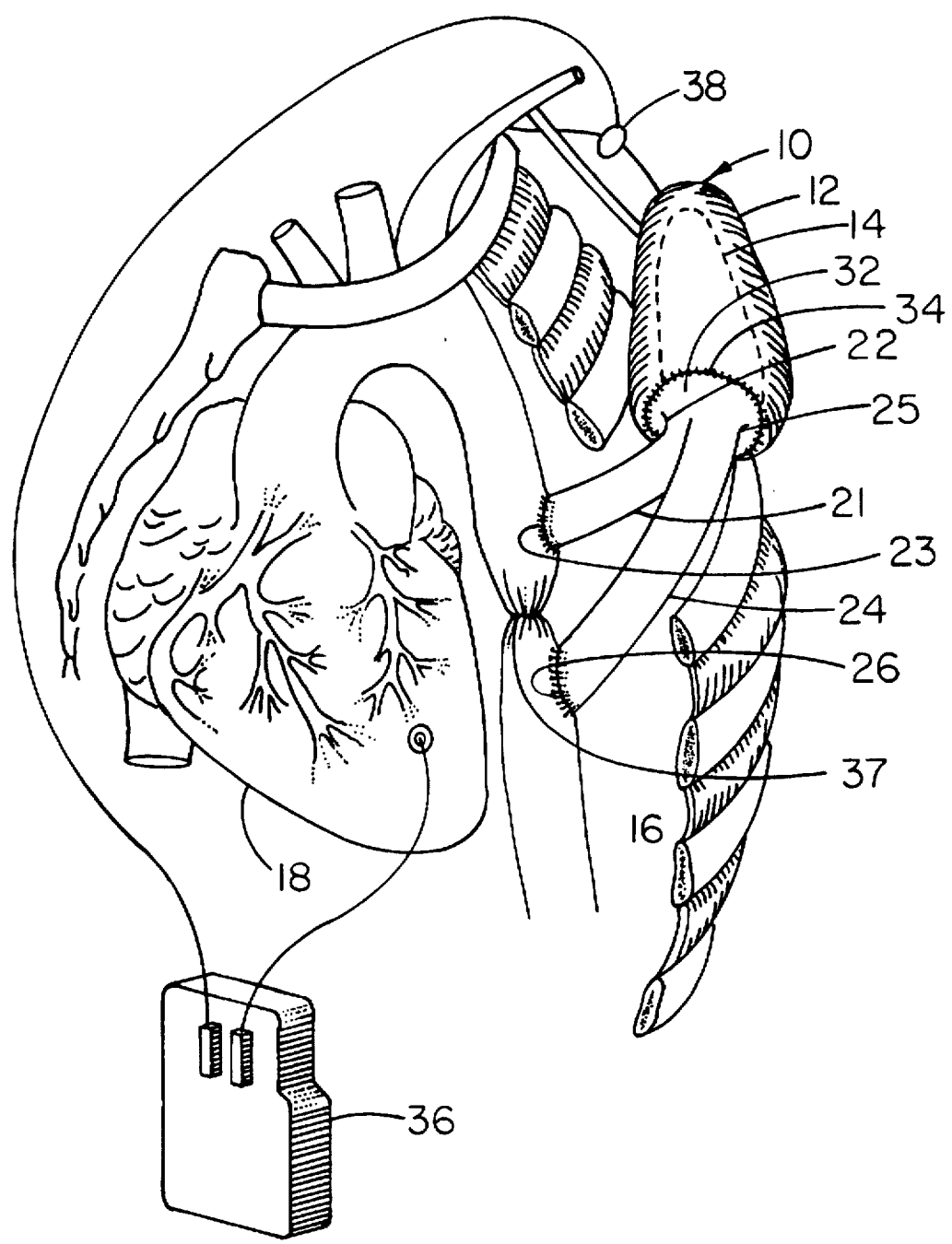
FIG. 1 describes a complete, functional LVAD.

FIG. 1 describes a typical LVAD 10 as made by either the prior art procedure or by the inventive procedure, wherein an SMV 12, formed previously around a temporary mandrel to create a cavity 14, is connected to a patient's aorta 16 by ends 23 and 26 of vascular grafts 21 and 24. Opposing first ends 22 and 25 of vascular grafts 21 and 24 are sewn to a synthetic sheet of circular patch material 32 which is in turn sewn to SMV 12 at suture line 34. Ligation 37 is placed about the aorta 16 between adjacent second ends 23 and 26 of vascular grafts 21 and 24 so that the flow of blood from the heart 18 is routed through the SMV 12. Pulsing of the SMV 12 is controlled by burst pulse generator 36 connected to the heart 18 and the thoracodorsal nerve 38.

The method of the prior art requires two surgical procedures to create the LVAD 10. The first surgery involves wrapping the freed end of the strip of latissimus dorsi muscle around a plastic mandrel to form the SMV. The second surgery to remove the mandrel from the SMV 12 includes the subsequent steps of sewing the circular patch material 32 to the SMV 12 and anastomosing the vascular grafts 21 and 24 to aorta 16 and the circular patch 32. After completion of these steps the LVAD is activated before closing the patient's chest. Because all of these various suture lines are created immediately preceding exposure of the LVAD to blood pressure and mechanical stress from the pulsing of the SMV 12, it is apparent that bleeding of the suture lines must be dealt with before the patient can be closed. Further, there is a substantial risk of disruption of this suture line in the first week following surgery, before significant healing of this suture line has had time to occur.

Figure 2A:
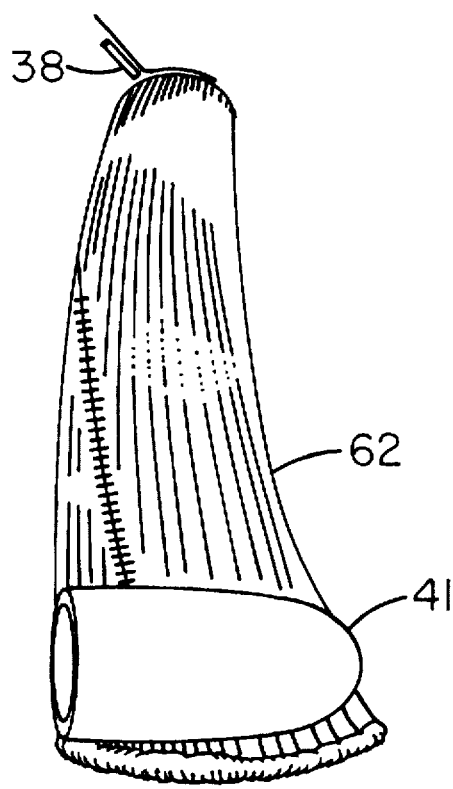
FIGS. 2A and 2B describe forming the SMV by wrapping latissimus dorsi muscle with or without optional pericardium around a mandrel.
Figure 2B:
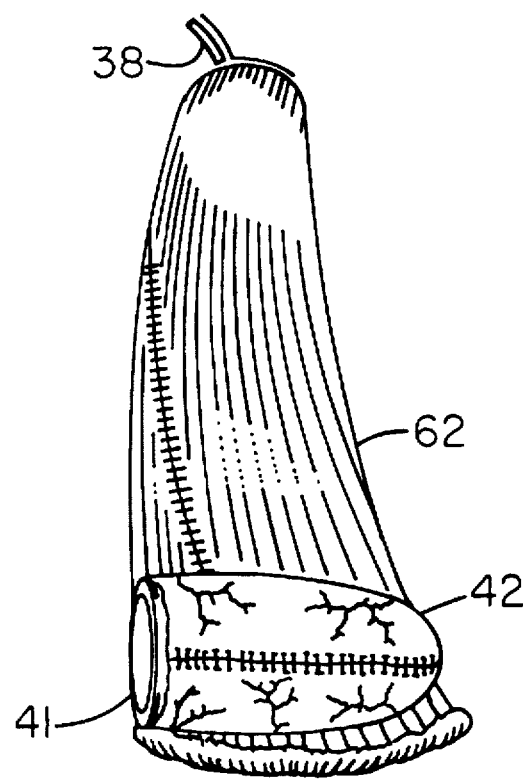
Figure 3:
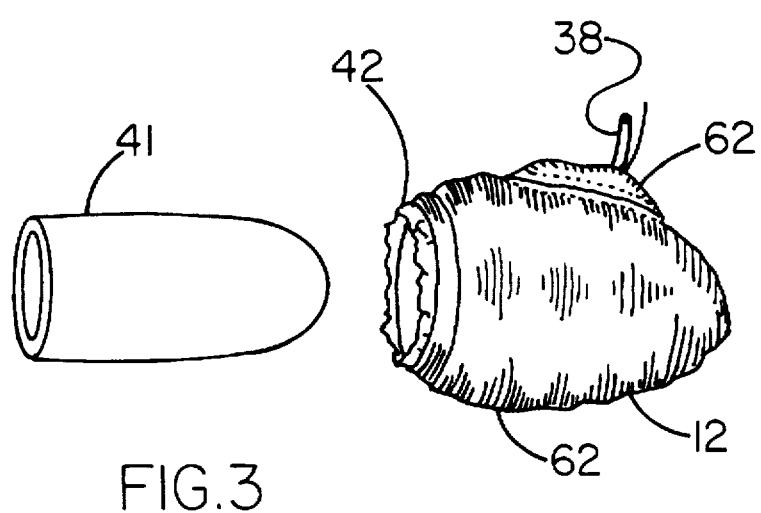
FIG. 3 describes removal of the mandrel from the SMV.

The method of the present invention is described beginning with FIG. 2A which describes the step of wrapping the latissimus dorsi muscle 62 around the mandrel 41; typically 2–2.5 wraps of latissimus dorsi muscle are used. FIG. 2B describes an alternative whereby a sheet of anterior pericardium 42, previously removed from between the phrenic nerves, is wrapped around mandrel 41 prior to wrapping the latissimus dorsi muscle 62 around mandrel 41 to create the SMV 12. As shown by FIG. 3, after the SMV 12 has been completed by sewing the latissimus dorsi muscle 62 to itself, mandrel 41 is removed from the SMV 12.

FIG. 4A describes a view of SMV 12 after removal of mandrel 41 and attachment of assembly 50 by sewing. Assembly 50 comprises vascular grafts 21 and 24 anastomosed to a piece of circular patch material 32 preferably in a leak-proof fashion whereby the anastomoses do not leak blood. Various methods of creating such a leak-proof assembly 50 are known. For example, porous PTFE vascular grafts may be anastomosed to porous PTFE patch material using porous PTFE sutures and the resulting suture line may be sealed with a medical grade silicone adhesive. Alternatively the suture line may be sealed by the use of a porous PTFE tape heat-sealed over the material edges adjacent to the seam line. According to still another alternative, a bifurcated vascular graft may be used wherein the large diameter portion of the graft is cut short and optionally deformed by flaring to provide the circumferential edge to be sewn to the SMV 12. Porous PTFE vascular grafts, cardiovascular patches and sutures are available from W. L. Gore and Associates, Flagstaff, Ariz. under the GORE-TEX® trademark. Porous PTFE materials of this type have a microstructure of nodes interconnected by fibrils and are made generally as described by U.S. Pat. Nos. 3,953,566 and 4,187,390 to Gore.

The edge of circular patch 32 is sewn at suture line 34 to the latissimus dorsi muscle 62 and to the pericardium 42 if pericardium is used.

FIG. 4B describes a cross sectional view of an alternative embodiment of the SMV 12 and attached assembly 50. In this embodiment the circular patch 32 has a pair of flanges 51 and 53 about its peripheral edge whereby inner flange 51 is sewn to the optional pericardium 42 and outer flange 53 is sewn to the latissimus dorsi muscle 62. Flanged patches of this type may be made by laminating sheets of porous PTFE together under heat and pressure while keeping the sheets separated at the edges during lamination to form the flanges. A ring of polyamide film such as Kapton (DuPont de Nemours, Wilmington, Del.) may be used temporarily as a separator during the lamination process. Alternatively the sheets may be laminated using a suitable adhesive such as medical grade silicone adhesive or a thermoplastic adhesive such as fluorinated ethylene propylene (FEP). Methods of making laminated porous PTFE articles are also taught by U.S. Pat. Nos. 4,385,093 and 4,478,665 to Hubis. Any method may be used as long as the resulting article is biocompatible and the laminations do not separate during use.

FIG. 5 shows the insertion of deflated balloon 45 into the SMV 12 via either vascular graft 21 or 24. Also as shown by this figure, after inflation of the balloon using syringe 47 via connecting tube 46, the inflated balloon 44 maintains the desired shape for the SMV 12. The balloon may be inflated using various media such as air, water or saline. The balloon may be made from any mechanically suitable biocompatible material; smaller balloons are used routinely in, for example, balloon catheters.

Figure 6:
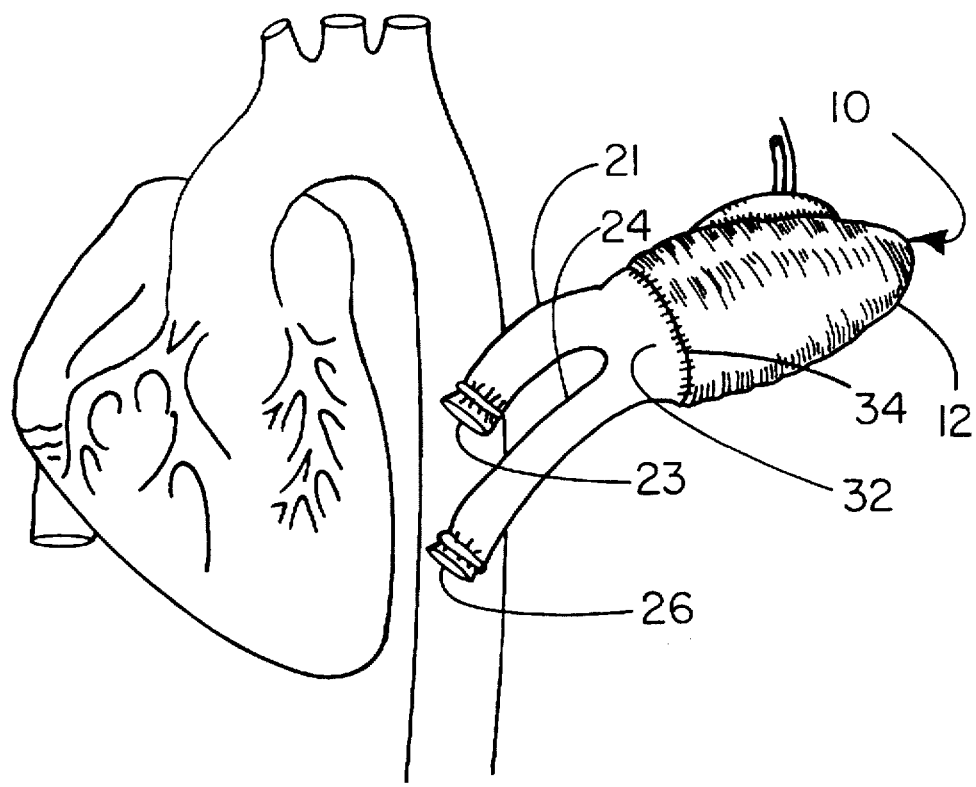
FIG. 6 describes the LVAD at the conclusion of the first surgery according to the method of the present invention.

FIG. 6 shows the completed LVAD 10 at the conclusion of the first surgery. Suture line 34 between patch 32 and the SMV 12 is allowed to heal during the initial three week healing period and subsequent six week stimulation period required for conversion of the fatigable Type II latissimus dorsi muscle to fatigue-resistant Type I muscle fibers. Second ends 23 and 26 of vascular grafts 21 and 24 are simply clamped off during this period.

In the subsequent second surgery, inflated balloon 44 is deflated 45 and removed via either vascular graft 21 or 24 through which it had previously been inserted. The use of a vacuum to aid in the deflation of the balloon may be advantageous in order in minimize the size of the balloon during removal. The cavity 14 of the SMV 12 may be visually inspected if desired by an endoscope inserted into the cavity 14 via vascular graft 21 or 24. As shown by FIG. 1, second ends 23 and 26 of vascular grafts 21 and 24 are anastomosed to aorta 16 which is then provided with ligation 37. The electrode leads are connected to generator 36, after which the generator is activated to begin function of the LVAD.

Figure 7A:
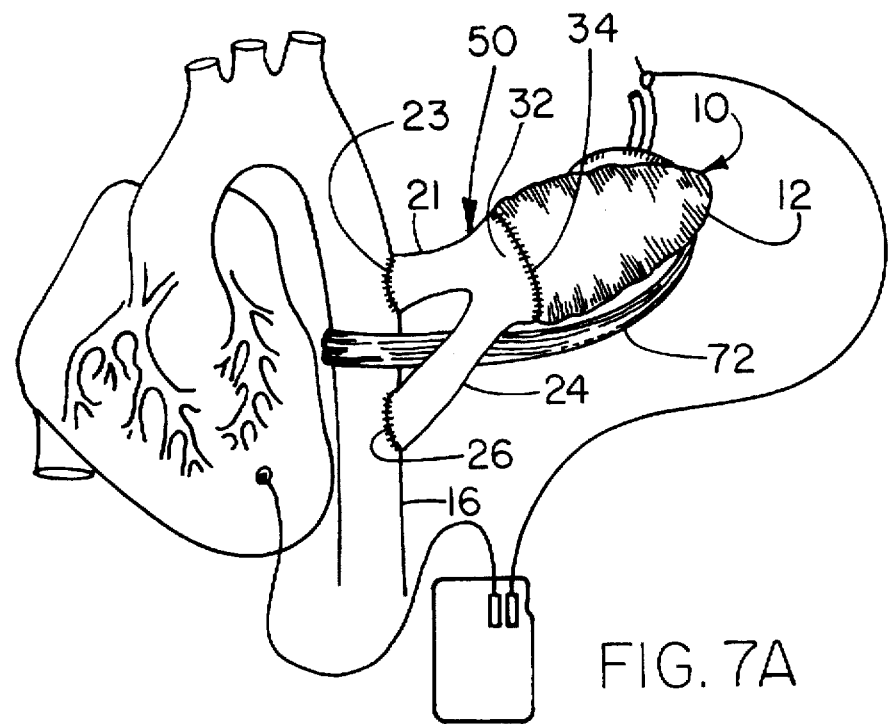
FIGS. 7A and 7B describe an alternative embodiment using a separate strip of latissimus dorsi muscle as an aortic clamp.
Figure 7B:
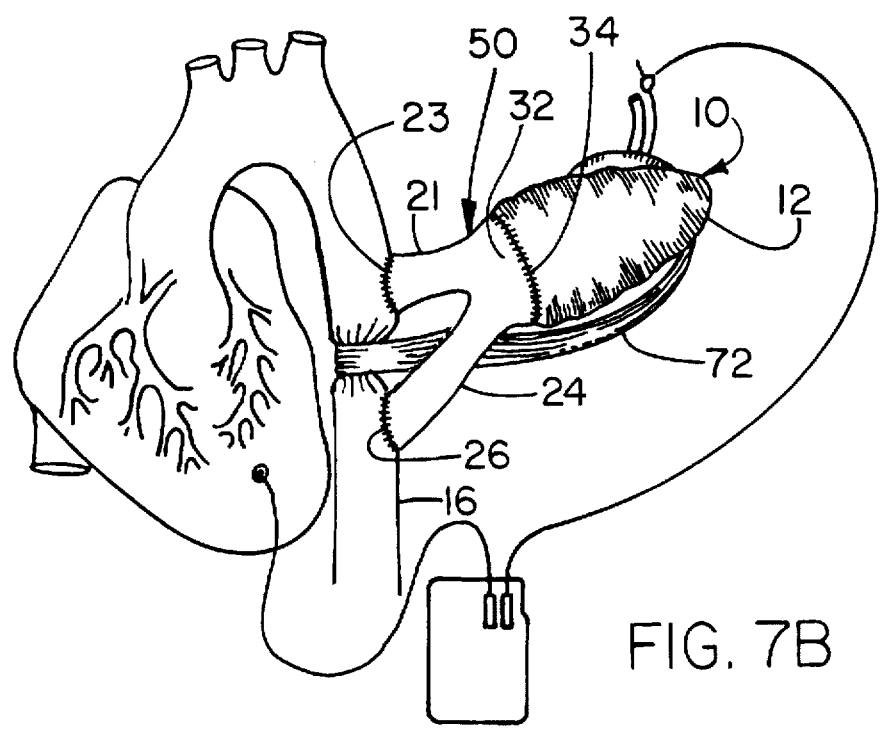

FIG. 7A describes an alternative embodiment wherein a separate strip 72 of latissimus dorsi muscle is wrapped around the aorta 16 between vascular graft second ends 23 and 26 and attached back to itself. Contraction of the strip 72 of latissimus dorsi muscle results in compression of aorta 16 as shown by FIG. 7B. This muscle strip 72 is intended to function synchronously with SMV 12 to cause external compression and at least partial occlusion of the aorta coordinated with contraction of the SMV. Optionally, muscle strip 72 may be provided with a protective tubular covering intended to prevent adhesions from surrounding tissue, the covering being placed coaxially about strip 72.

Figure 8A:
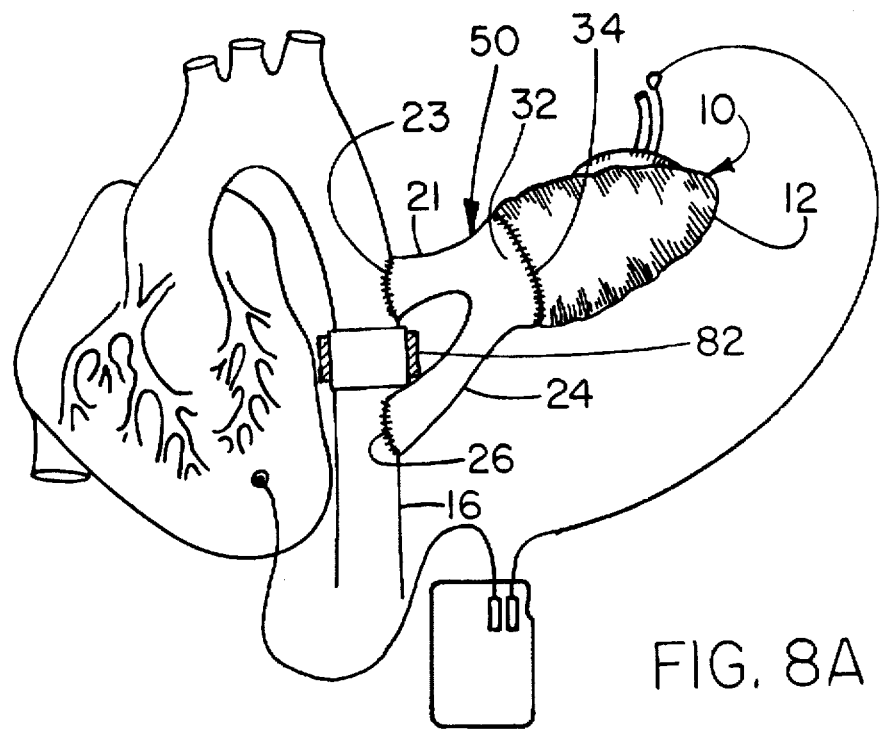
FIGS. 8A and 8B describe an alternative embodiment using a mechanical device as an aortic clamp.
Figure 8B:
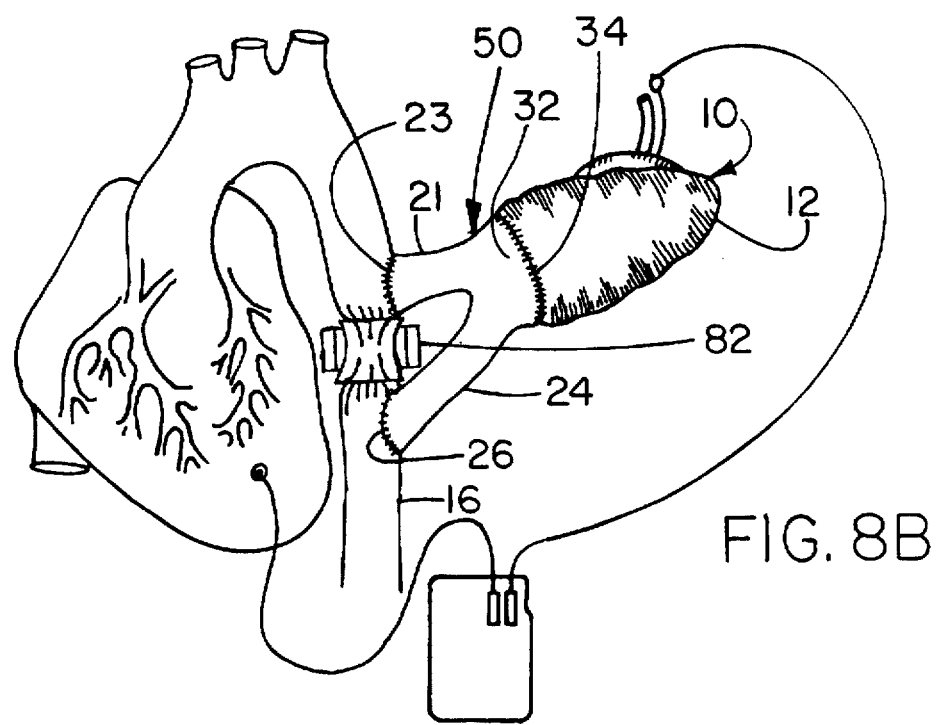

As described by FIGS. 8A and 8B it is envisioned that both of the alternative functions of the separate muscle strip 72 shown by FIGS. 7A and 7B may be accomplished by mechanical clamping device 82 (preferably pneumatic or hydraulic) controlled by a pacemaker or defibrillator type of generator depending on whether clamping device is desired to function simultaneously with the LVAD or in the event of failure of the LVAD. Alternatively, the mechanical clamping device 82 may be controlled to accomplish both of these functions. Optionally, the aorta 16 may be protected by a thin layer of protective synthetic material underneath the mechanical clamping device 82 where the device 82 is attached to the aorta 16.

Figure 9:
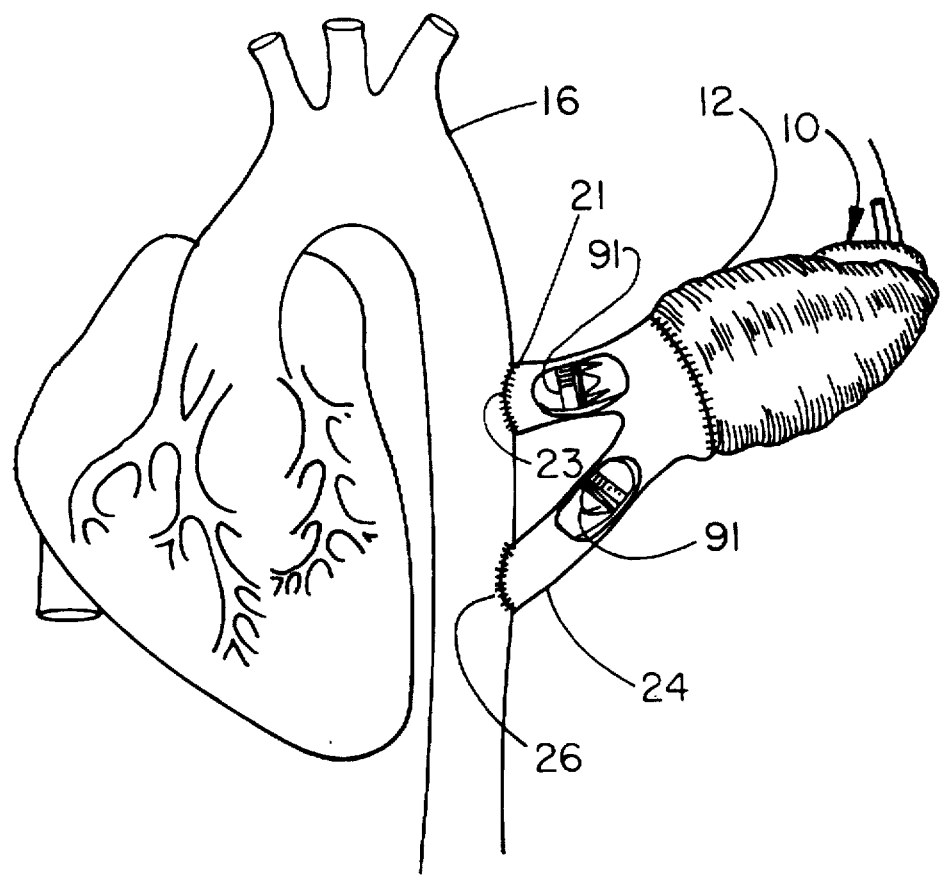
FIG. 9 describes an alternative embodiment wherein valves are incorporated into the vascular grafts connecting the SMV to the aorta.

In still another alternative shown by FIG. 9, the vascular grafts 21 and 24 may be provided with valves 91 to control the direction of blood flow through the LVAD 10. Prosthetic heart valves of suitable diameter for the vascular grafts may be used as the valves 91. The use of valves 91 may eliminate the need to ligate the aorta.

Figure 10:
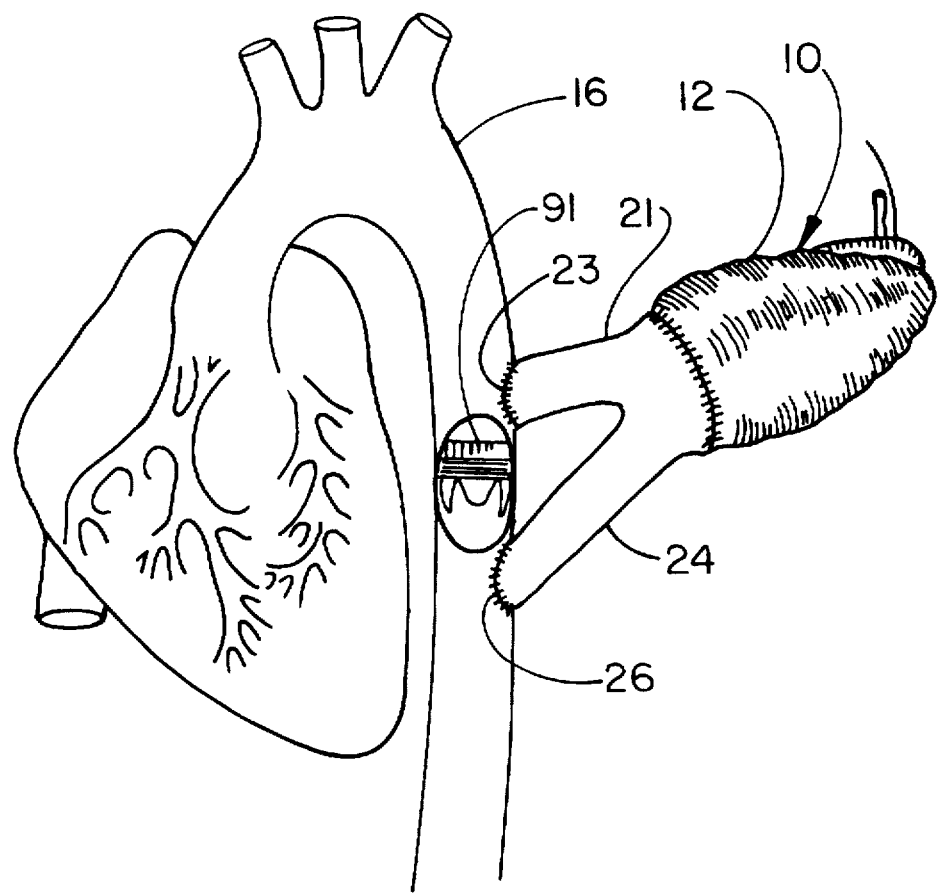
FIG. 10 describes an alternative embodiment wherein a prosthetic heart valve is fitted into the aorta at a location between the ends of the pair of vascular grafts connecting the SMV to the aorta.

FIG. 10 describes another alternative whereby a prosthetic heart valve 91 may be fitted into the aorta 16 between the anastomosed second ends 23 and 26 of vascular grafts 21 and 24. In this embodiment as well, the use of valve 91 is anticipated to eliminate the need to ligate the aorta or to close it synchronously by external compression.

Figure 11A:
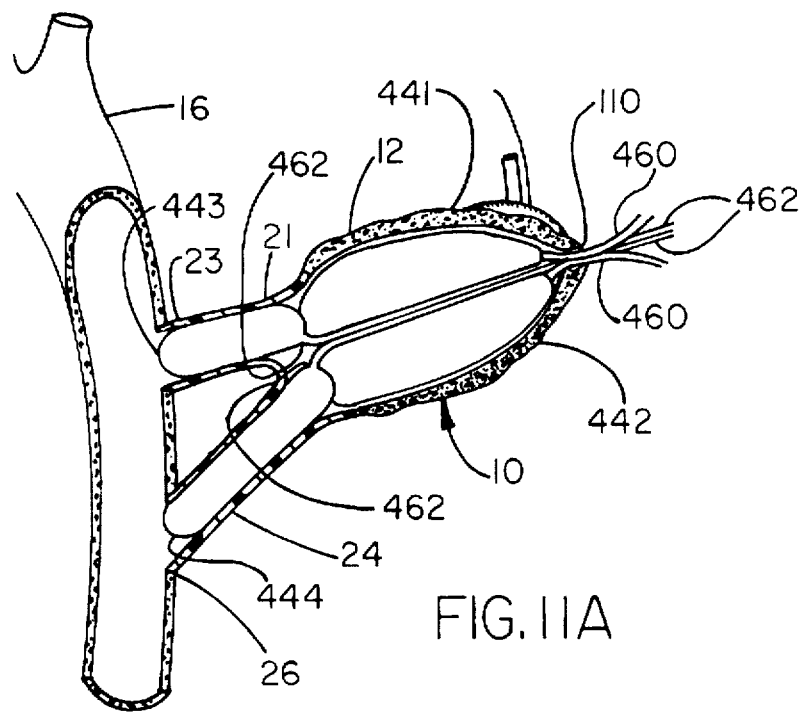
FIG. 11A describes an alternative embodiment wherein the LVAD procedure is accomplished in a single major surgery allowing the vascular graft anastomoses to the aorta to be created during the first surgery; the grafts are occluded during the subsequent healing and SMV stimulation period using balloons which may be deflated and removed subcutaneously via their inflation tubes extending through the apex of the SMV along with the balloon or balloons that supported the SMV during the healing and stimulation period.

Still another alternative embodiment eliminates the need for the second major surgical procedure. According to this embodiment the anastomoses of the second ends of the vascular grafts to the aorta are made prior to concluding the first surgery. This is possible by inserting one or more inflatable balloons into a small opening 110 in the apex of the SMV 12 opposite the vascular grafts 21 and 24 as shown by FIG. 11A. Balloons extend into the vascular grafts to maintain them in an occluded condition until it is intended to activate the LVAD. Preferably, each vascular graft 21 and 24 is occluded by an individual balloon 443 and 444 which is fitted into correct position lengthwise so that when inflated it fills the respective vascular graft with little or no extension into the aorta 16 and without substantially interfering with aortic blood flow during the healing period. The position of the opposite ends of the vascular graft occluding balloons 443 and 444 is less critical but should be near or slightly protrude into the SMV 12. After the vascular graft occluding balloons 443 and 444 are correctly positioned and inflated via their inflation tubes 462, third and fourth balloons 441 and 442 are placed into the SMV 12 and inflated via inflation tubes 460 to maintain the shape of the SMV 12 during healing. By using third and fourth balloons 441 and 442, the inflation tubes 462 of the vascular graft occlusion balloons 443 and 444 may be located between the third and fourth balloons 441 and 442 filling the SMV 12 thereby reducing the risk of interior abrasion of the SMV 12 during healing and stimulation. Alternatively, a single balloon might be used in place of the separate third and fourth balloons 441 and 442 if the inflation tubes 462 of the vascular graft occluding balloons 443 and 444 are routed so as to avoid damage to the interior of the SMV 12 during the healing and stimulation period. The inflation tubes 460 and 462 of all four balloons 441-444 extend through the small opening 110 in the SMV 12, whereby they remain located subcutaneously during healing and are easily accessible for subsequent deflation and removal of the balloons. The small opening 110 may be easily closed by suturing immediately preceding activation of the LVAD. By this method the second major surgery to anastomose the vascular grafts is eliminated.

Figure 11B:
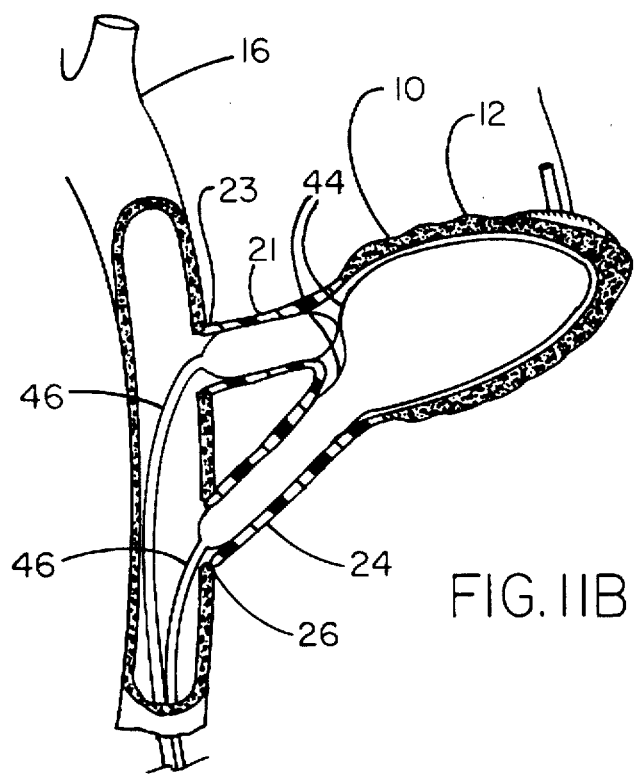
FIG. 11B describes a variation of the embodiment shown by FIG. 11A wherein the balloons occluding the vascular grafts and supporting the SMV during the healing and stimulation period may be removed by their inflation tubes via the distal vascular system.

In an alternative embodiment of the procedure described by FIG. 11A, FIG. 11B describes a variation wherein the inflation tubes of the inflatable balloon or balloons extend distally through the vascular system to allow subsequent deflation and removal via, for example, a femoral artery. This alternative embodiment also allows the second ends 23 and 26 of the vascular grafts 21 and 24 to be anastomosed to the aorta 16 during the first surgery and thereby avoids the second major surgery.

In another embodiment which is useful as a variation of the previously described alternatives, it is anticipated that the SMV 12 may be connected to the aorta 16 with a single vascular graft 20 used alternately to fill and discharge the SMV 12 synchronously with the function of the heart. This embodiment is shown generally by FIG. 12. Heart valves (not shown) may be used advantageously in this embodiment in similar manners to those shown by FIGS. 9 and 10.

Figure 13:
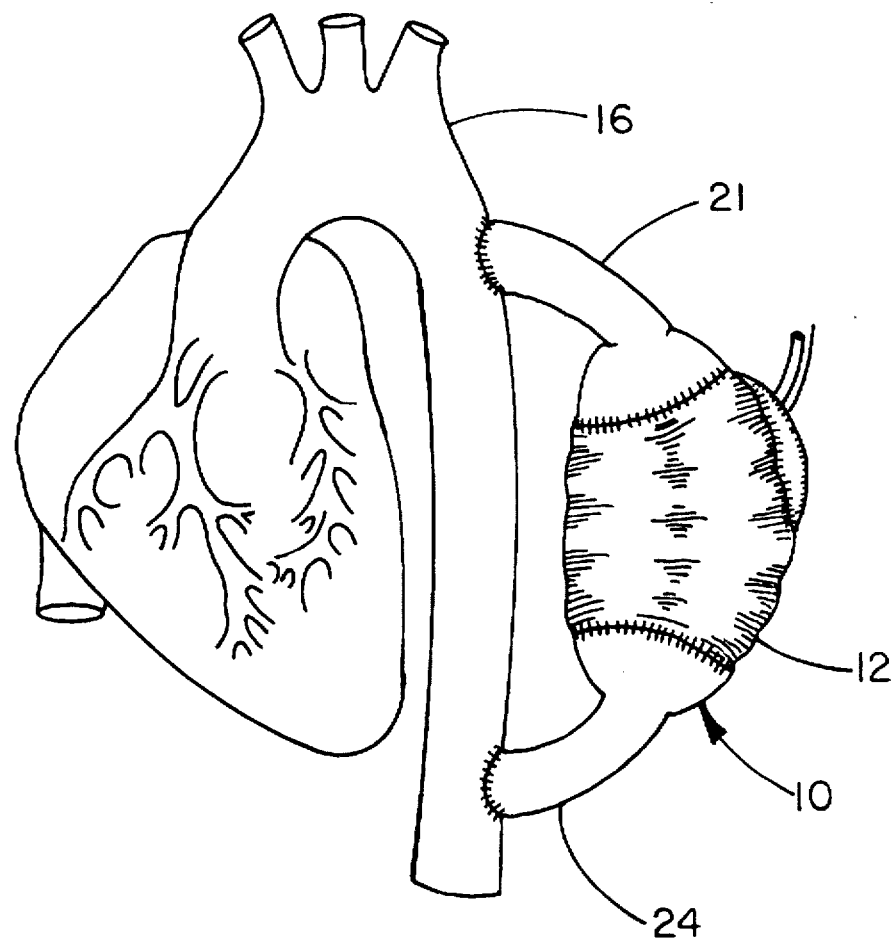
FIG. 13 describes an embodiment wherein the SMV is fashioned to function as an inline pump wherein the inlet and outlet vascular grafts are at opposite ends of the SMV.

FIG. 13 describes an embodiment wherein the SMV is fashioned to function as an inline pump wherein the inlet and outlet vascular grafts 21 and 24 are at opposite ends of the SMV 12. Heart valves (not shown) may also be used advantageously in this embodiment in similar manners to those shown by FIGS. 9 and 10.

Various other inventive methods have been devised for providing a shape-maintaining form that is insertable into a newly constructed LVAD to which the vascular grafts have been attached, and removable from the LVAD after a healing period. As with the previously described inflatable and deflatable balloon used as the shape-maintaining form, the following alternatives are all expandable and collapsible forms, meaning that the volume of the form is variable depending on whether the form is collapsed and contained within an insertion and removal device such as a catheter, or released from the insertion and removal device thereby allowing it to expand to a substantially larger volume.

Figure 14A:
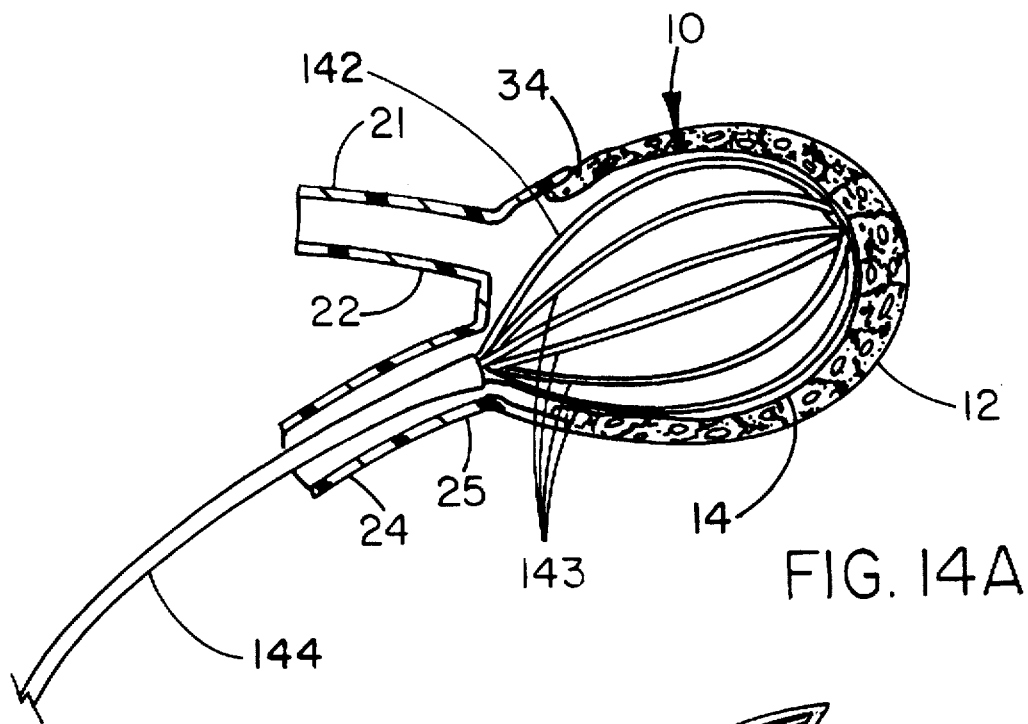
FIGS. 14A and 14B describe an alternative embodiment of the present invention wherein a shape-maintaining form for use during healing of a newly created LVAD is provided in the form of an expandable and collapsible wire frame.
Figure 14B:
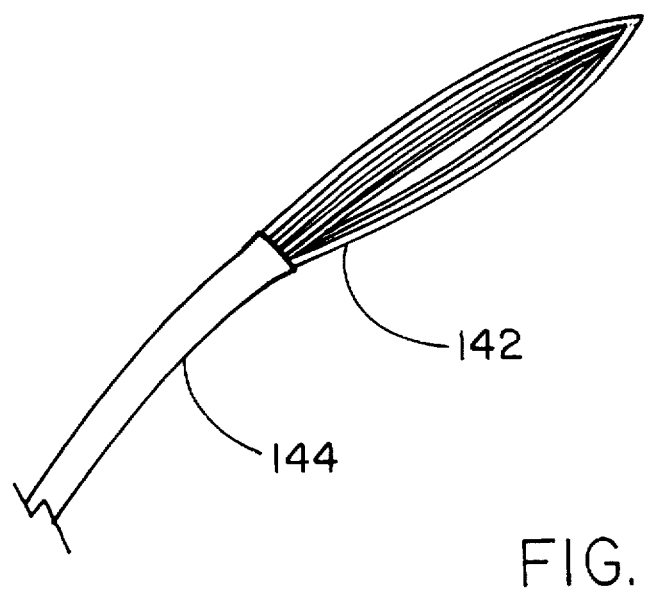
Figure 15A:
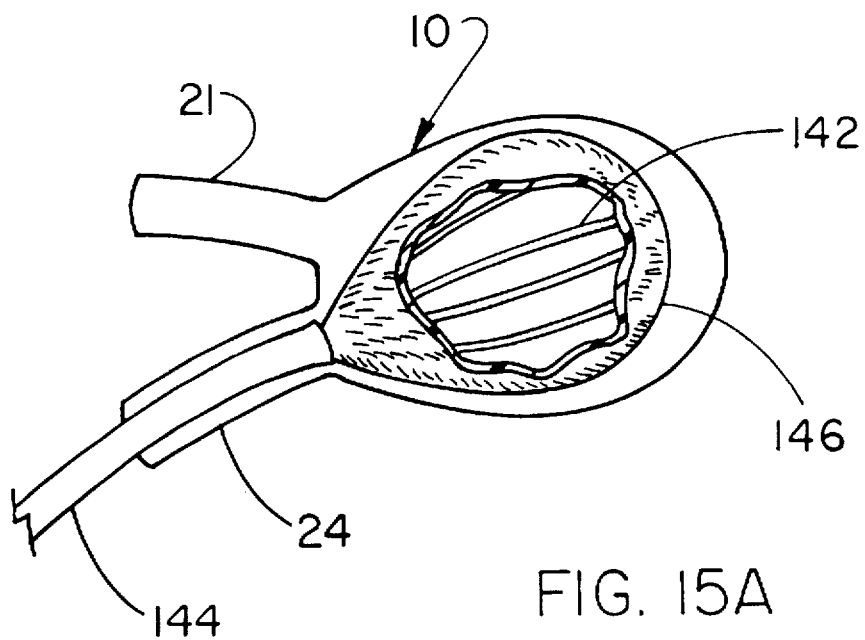
FIGS. 15A and 15B describe an alternative embodiment to that of FIGS. 14A and 14B wherein the wire frame is provided with a flexible covering.
Figure 15B:
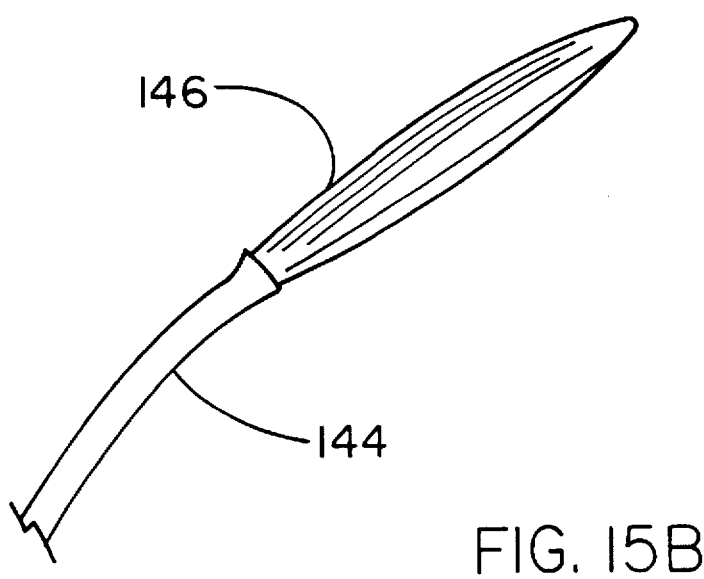

FIGS. 14A and 14B describe an expandable and collapsible wire frame 142 that may be inserted and removed via catheter device 144. The wire frame 142 has individual elements 143 that are arranged in directions substantially parallel to the length of the LVAD 10 (as opposed to having a substantially circumferential orientation). The wire frame 142 expands to the desired shape after release from the catheter 144 as shown in FIG. 14A; the wire frame 142 is subsequently collapsed into the catheter 144 when it is desired to remove it from the LVAD 10 prior to activation of the LVAD. In a preferred variation described by FIGS. 15A and 15B, the wire frame 142 is provided with a covering 146 which is also expandable and collapsible with the wire frame. It is believed that the use of a such a covering will provide an improved ability to maintain the desired shape for the LVAD during healing. A suitable covering material is porous expanded PTFE sheet material as described previously. The use of porous expanded PTFE is believed to be preferred because of its strength and biocompatibility and because the pore structure can be provided in various fibril lengths to control tissue ingrowth as desired.

Figure 16A:
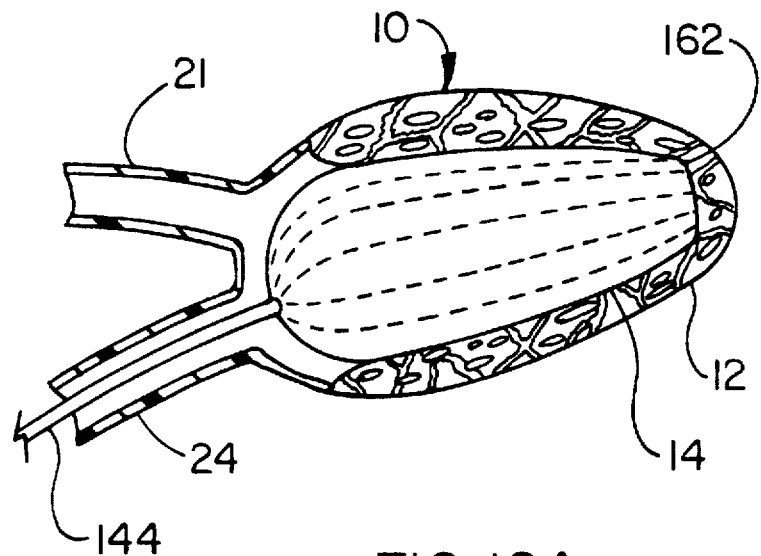
FIGS. 16A and 16B describe an alternative embodiment wherein a semi-rigid plastic shape-maintaining form is provided which is vacuum collapsible.
Figure 16B:
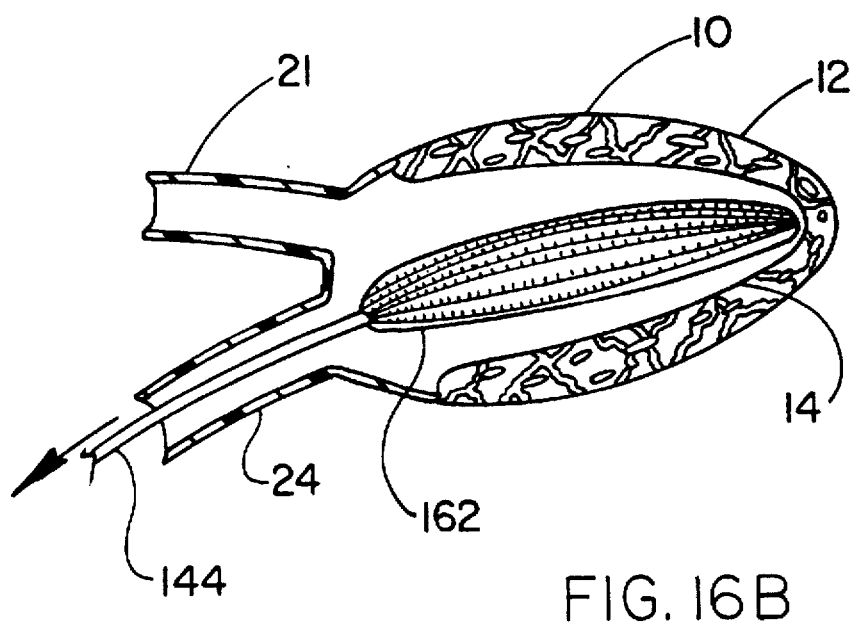

FIGS. 16A and 16B show a hollow, semi-rigid plastic form 162 having ridges or stress relief lines that enable it to be expanded by the use of pressure and subsequently collapsed by the application of a vacuum to its interior when it is desired to remove it from the formed LVAD 10. The collapse of the form 162 by the application of vacuum allows it to be removed through one of the vascular grafts 21 or 24 connecting the LVAD 10 in the general manner previously described for removal of a deflated shape-forming balloon 45.

Figure 17A:
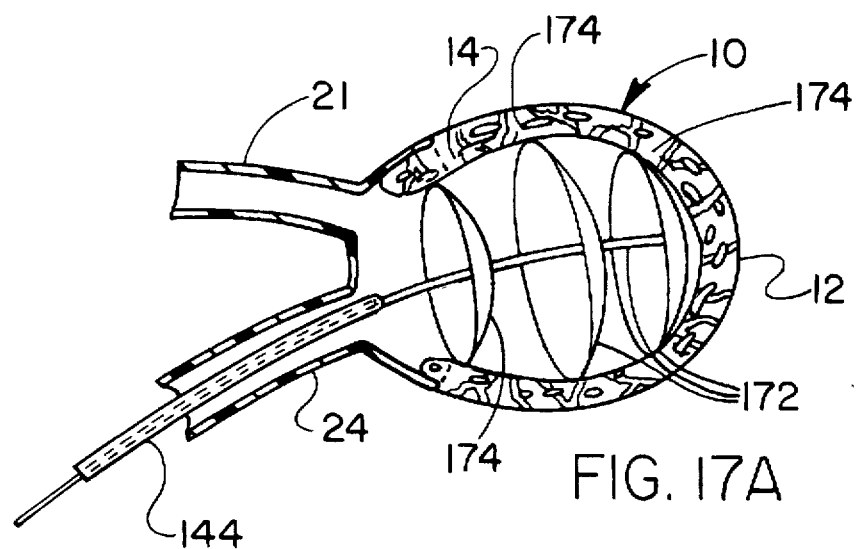
FIGS. 17A, 17B and 17C describe an alternative embodiment wherein a shape-maintaining form is provided having evertable and collapsible cone elements.
Figure 17B:
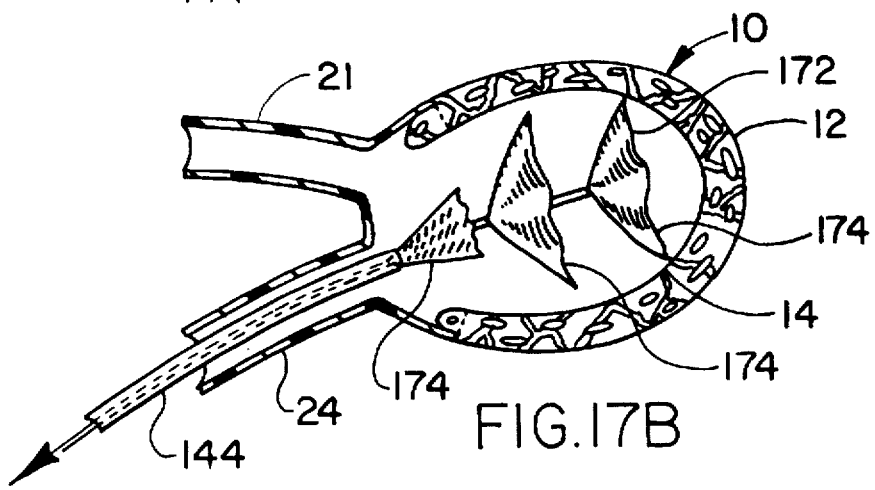
Figure 17C:
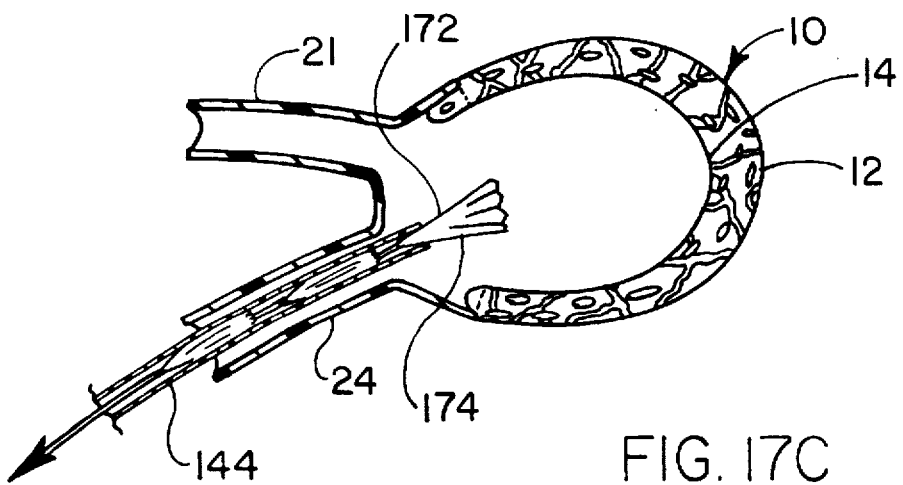

FIGS. 17A, 17B and 17C describe a collapsible cone form 172 wherein the use of at least three evertable and collapsible cone elements 174 provide the desired shape for the LVAD 10 during the healing period. As with the wire frame shape-maintaining form 142 of FIGS. 15A and 15B, the collapsible cone form 172 may be provided with a flexible and collapsible covering 146 of the same type (not shown). The collapsible cone form 172 differs primarily from the wire frame 142 in that the cone elements 174 that exert a supporting force against the interior of the LVAD 10 are substantially circumferentially oriented with respect to the LVAD 10 rather than substantially longitudinally oriented.

Figure 12:
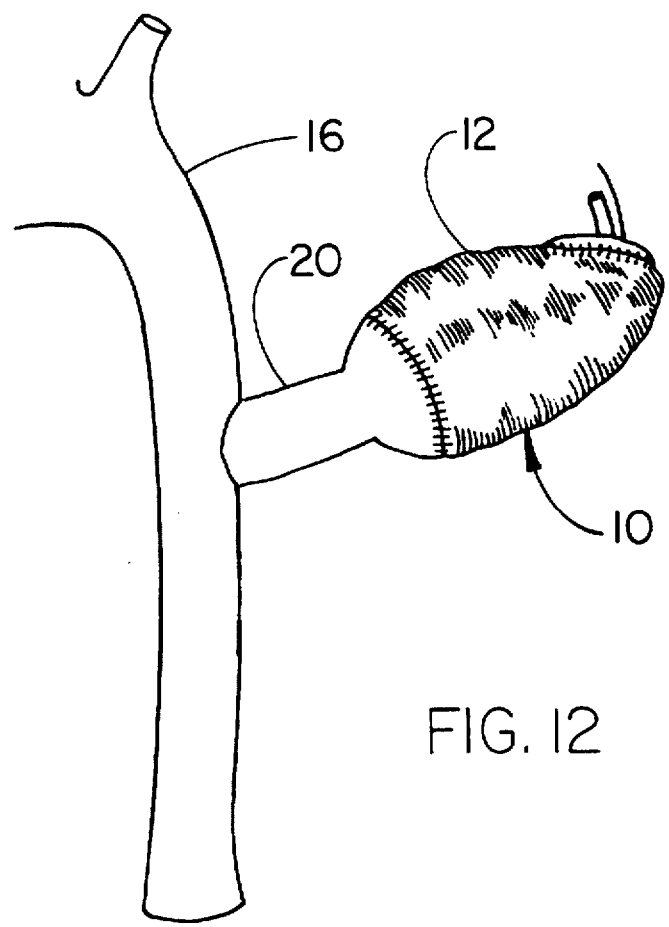
FIG. 12 describes an embodiment using a single vascular graft to connect the SMV to the aorta.
Figure 18A:
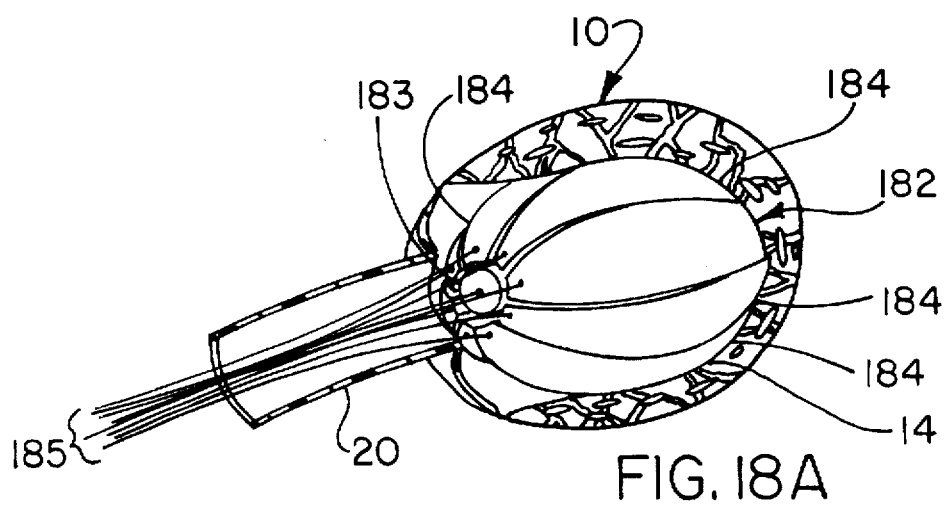
FIGS. 18A, 18B, and 18C describe an alternative embodiment of a shape-maintaining form having a multiplicity of sequentially, individually removable segments.
Figure 18B:
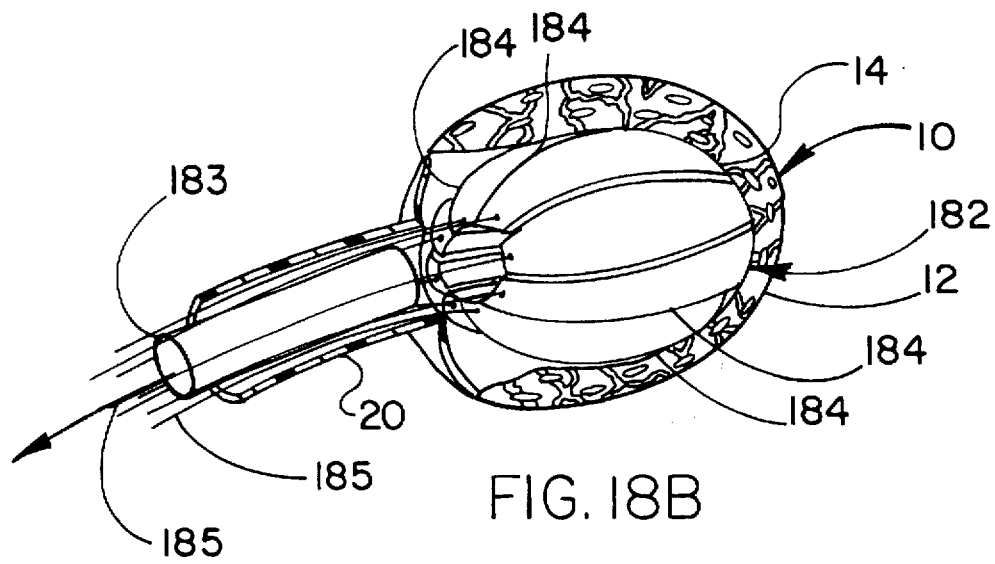
Figure 18C:
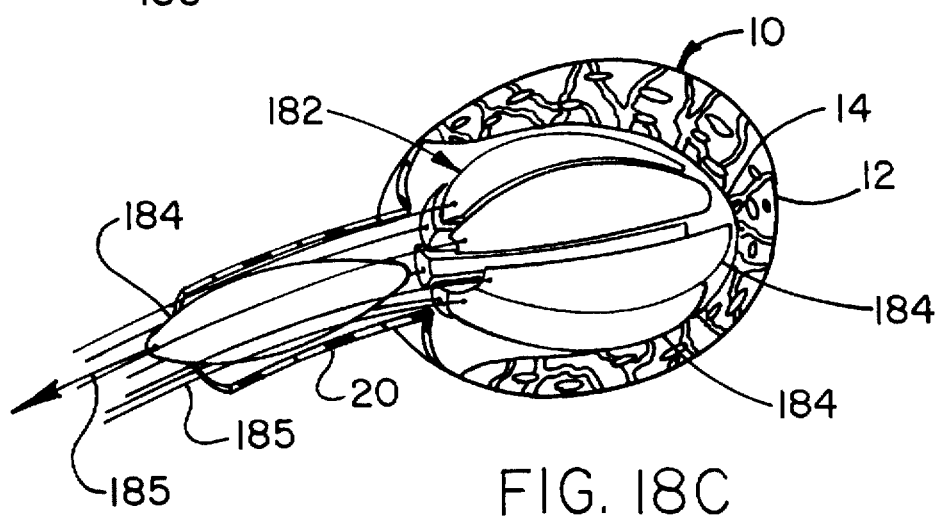

According to another alternative shown by FIGS. 18A, 18B and 18C, a removable, segmented shape-maintaining form 182 may be constructed of peripheral segments 184 fitted together to achieve the desired form, wherein peripheral segments 184 are individually removable via removal means such as, for example, connecting strings 185 extending through vascular graft 20. While the embodiment shown incorporates a single vascular graft 20 as also shown by FIG. 12, it is apparent that this embodiment may also be provided with a pair of vascular grafts (as shown by grafts 21 and 24 of FIG. 1) and that the segments 184 may be set up to be removable through either graft. The segments 184 are adequately small to allow their sequential, individual removal from the LVAD 10 through one of the connecting vascular grafts 21 or 24. FIGS. 18A, 18B and 18C describe such a removable, segmented form 182 which includes an optional cylindrical core segment 183 which may be the first removable segment as shown by FIG. 18B, and a series of peripheral segments 184 which are subsequently removable on an individual and sequential basis as shown by FIG. 18C. Core segment 183 may optionally be provided with a locking mechanism which secures the various segments together during healing and which is released by, for example, applying tension to the removal means 185. Alternatively, the removable, segmented form 182 may be made to be hollow so that a cylindrical core segment 183 is not used, wherein the peripheral segments 184 fit together in a removable fashion about a hollow center space.

Figure 19A:
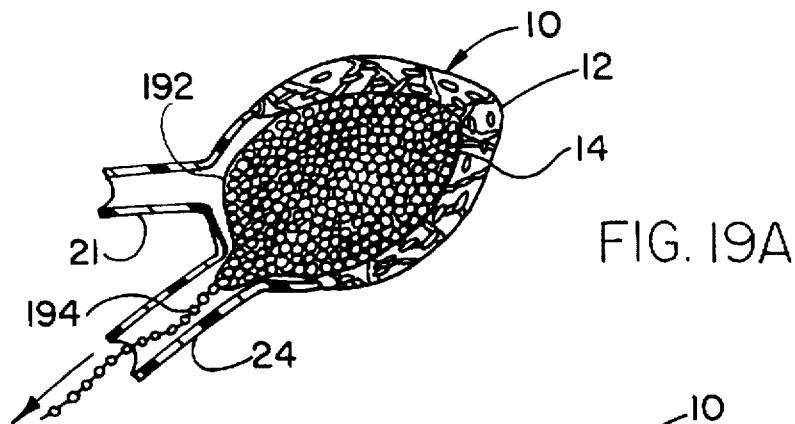
FIGS. 19A, 19B, 19C and 19D describe an alternative embodiment of a shape-maintaining form wherein a flexible bag is provided for the containment of a length of flexible material which is length-wise insertable into and removable from the bag and wherein the bag is subsequently removable.
Figure 19B:
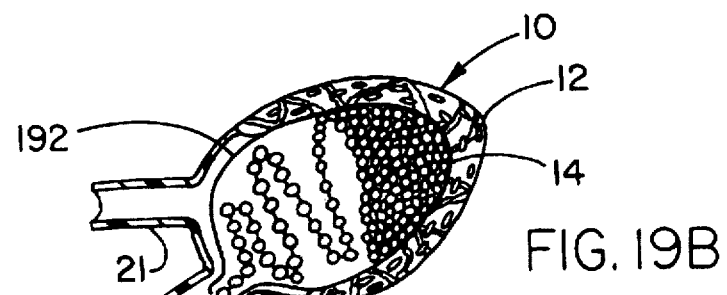
Figure 19C:
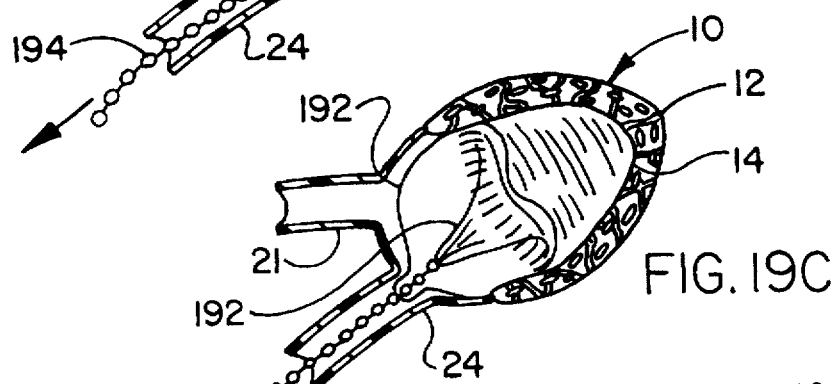
Figure 19D:
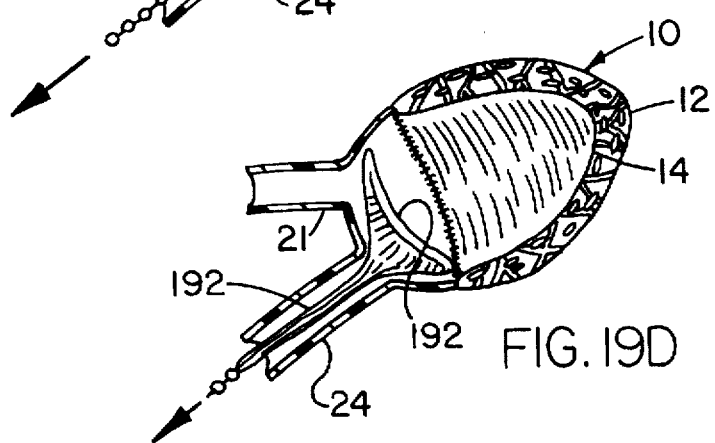

In another alternative described by FIGS. 19A, 19B, 19C, and 19D, the expandable and collapsible form can be provided as a bag 192 made from biocompatible material such as porous expanded PTFE wherein the bag 192 is filled with a length of bead-chain 194 which is easily removable through one of the connecting vascular grafts 21 or 24. Bead-chain 194 is comprised of a series of beads which may be made from a relatively light and biocompatible material such as polypropylene or PTFE, strung on a filament such as fiber or suture made from porous expanded PTFE. The end of the bead-chain 194 opposite the end from which tension is applied for removal may be attached to the bag 192 opposite the bag opening as shown by FIGS. 19C and 19D, which allows removal of the bead-chain 194 to conclude with removal of the containment bag 192 as well. As an alternative to the length of bead-chain 194, a length of cord having an approximately round cross section may be used as a space-filling material to fill bag 192, the cord also being removable lengthwise from the bag in the same fashion. Various other flexible, lengthwise removable materials may be possible alternatives to is the cord or bead-chain. Likewise, the use of individual, unconnected components such as a multiplicity of individual beads may be possible as a fill material for use with a containment bag 192 wherein the individual components are removed from within the bag by the use of a vacuum tube. While FIGS. 19A–19D describe the bead-chain as being removable through a connecting vascular graft, the bead-chain or alternative material may be made to be removable through an opening in the apex of the LVAD such as opening 110 shown by FIG. 11A.

Figure 20A:
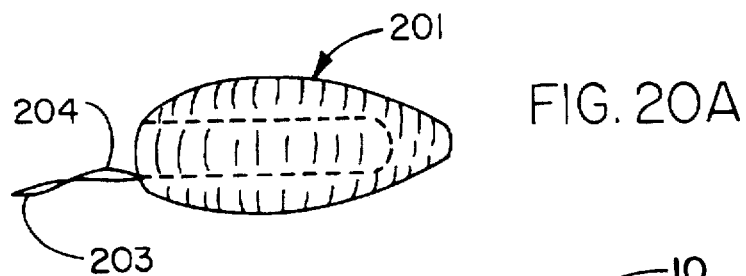
FIGS. 20A, 20B, 20C and 20D describe an alternative embodiment wherein a tape-wrapped shape-maintaining form is provided from a length of tape, with the tape being semi-adhered to itself and lengthwise removable from the interior of the form.
Figure 20B:
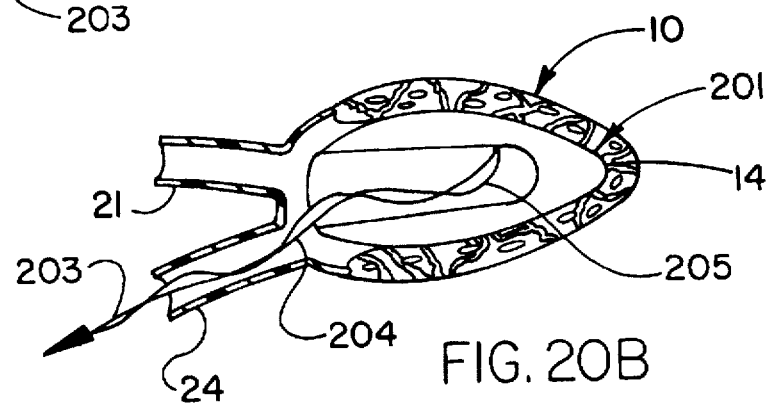
Figure 20C:
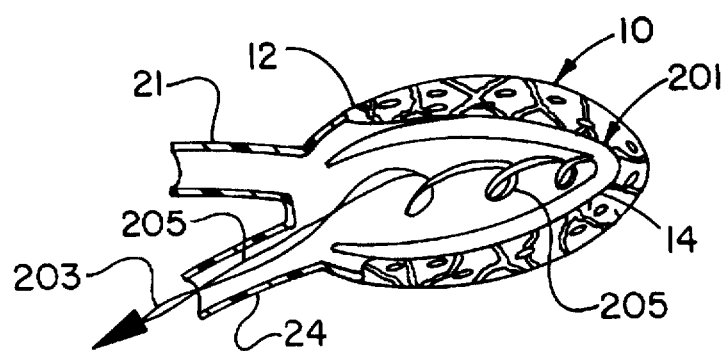
Figure 20D:
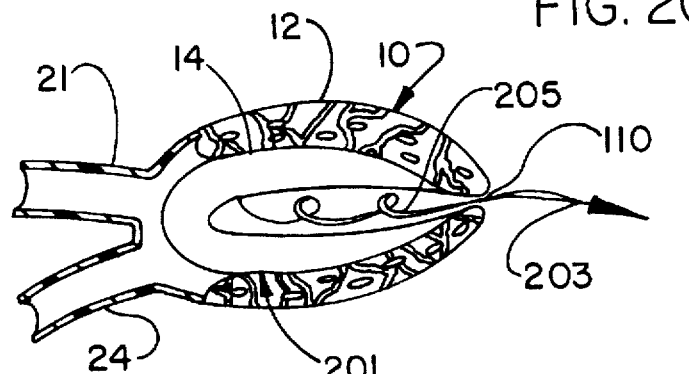

According to another embodiment shown by FIGS. 20A, 20B, 20C and 20D, a tape-wrapped shape-maintaining form 201 may be made from a long length of tape 205 wrapped about a mandrel which is in itself removable from the covering tape 205 after the desired shape of form 201 has been achieved by the wrapping of tape 205 onto the mandrel (not shown). A length of tape 204 adjacent to the first end 203 of the tape 205 is left free in order to provide an end 203 to which tension may be applied when it is subsequently desired to remove the tape-wrapped form 201 from the interior of the LVAD 10 after the healing period. As described by FIGS. 20B and 20C, the tape-wrapped form 201 is removable when desired by applying tension to end 203 of the tape 205 which extends from the interior of the form 201, thereby causing unwinding of the tape 205 from the inside of the form 201 and consequent complete removal of the form 201 as the tape 205 continues to unwind. FIG. 20D describes an alternative wherein the tape is removable via a small opening 110 located in the apex of the LVAD 10. The tape 205 should be of a biocompatible material such as porous expanded PTFE film and should be semi-adhered to itself so that it forms a cohesive form 201 in the desired shape which subsequently allows unwinding when a relatively small amount of tension is applied to the tape 205 during removal. The tape may be semi-adhered to itself by the use of a suitable adhesive or by applying a controlled amount of heat to the tape-wrapped form 201 after completion of wrapping to cause a limited a mount of thermal bonding to occur. The tension required for removal of the tape 205 from the interior of the LVAD 10 must be appreciably less than the break strength of the tape 205.

Figure 21A:
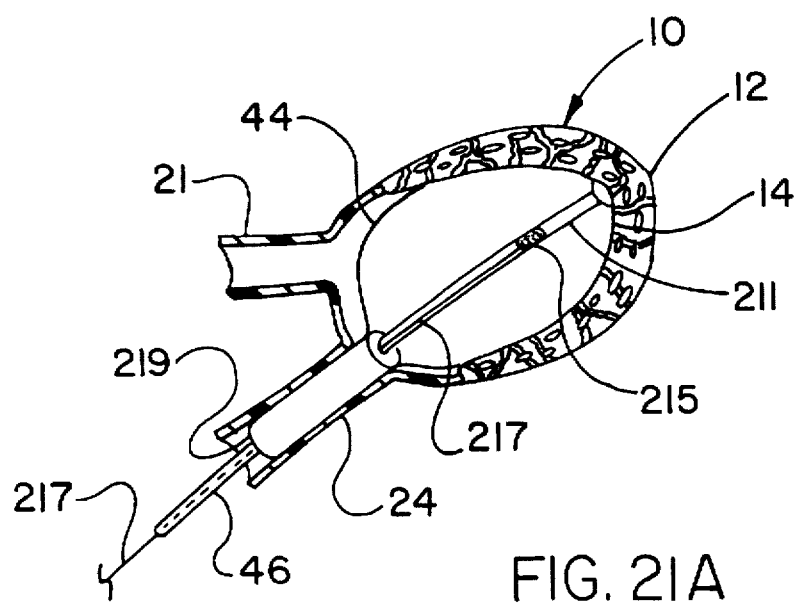
FIGS. 21A and 21B describe an alternative embodiment wherein a shape-maintaining inflatable and collapsible balloon is provided, the balloon having a stylet to aid in removability. The balloon is optionally provided with a pressure sensor.
Figure 21B:
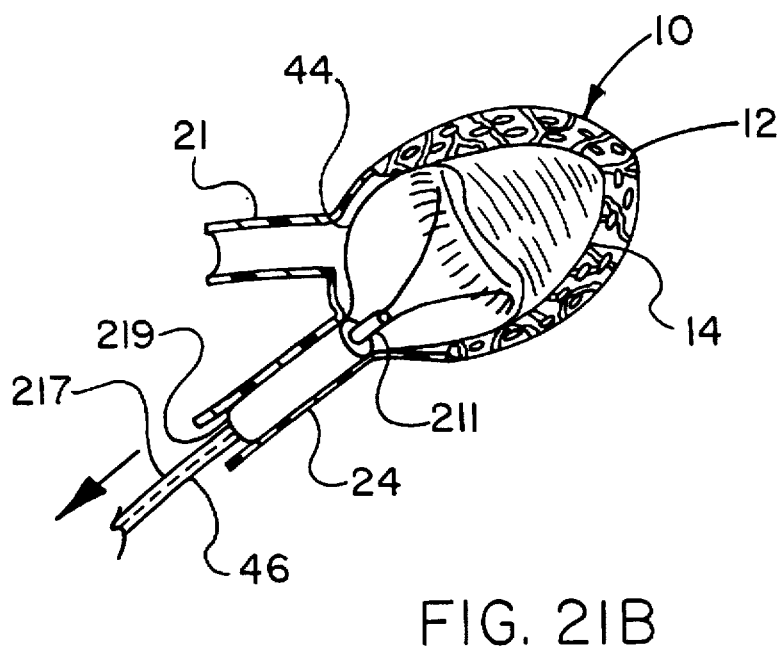

FIGS. 21A and 21B describe another embodiment wherein an inflated balloon 44 is used as the shape-maintaining form. This is similar to the embodiment of FIG. 5 with the addition of stylet 211 attached to the end of balloon 44 opposite the inflation tube 46. A sealing plug 219 made from a compliant material such as a silicone may be used to occlude the vascular graft around the inflation tube 46 if desired. As shown by FIG. 21B, stylet 211 facilitates eversion of the balloon 44 during its deflation, collapse and subsequent removal via inflation tube 46 within vascular graft 21 or 24, by the application of tension to the end of stylet 211 exterior to the LVAD 10. Optionally, the stylet 211 may contain a pressure sensor 215 and associated electrical lead 217 to allow the pressure within the balloon 44 to be monitored and controlled during the time the balloon 44 is used to maintain the shape of the LVAD 10.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. A method of maintaining the shape of a left ventricular assist device after forming the device and attaching one end of a vascular graft to the device, comprising:
   a) inserting an expandable and collapsible balloon into the left ventricular assist device, wherein said balloon contains a pressure sensor;
   b) expanding the balloon to fill space within the left ventricular assist device;
   c) allowing a period of time for healing of the left ventricular assist device; and
   d) collapsing the balloon and removing the balloon from the left ventricular device.

2. A method according to claim 1 wherein the balloon contains a stylet that aids in the removal of the balloon following deflation.

3. A method of maintaining the shape of a left ventricular assist device after forming the device and attaching one end of a vascular graft to the device, comprising:
   a) inserting an expandable and collapsible form into the left ventricular assist device, wherein said form is a wire form;
   b) expanding the form to fill space within the left ventricular assist device;
   c) allowing a period of time for healing of the left ventricular assist device; and
   d) collapsing the form and removing the form from the left ventricular device.

4. A method according to claim 3 where the wire form has a flexible outer covering.

5. A method according to claim 4 wherein the flexible outer covering is porous PTFE.

6. A method of maintaining the shape of a left ventricular assist device after forming the device and attaching one end of a vascular graft to the device, comprising:
   a) inserting an expandable and collapsible form into the left ventricular assist device, wherein said form is collapsible by the application of a vacuum to an interior space within the form;
   b) expanding the form to fill space within the left ventricular assist device;
   c) allowing a period of time for healing of the left ventricular assist device; and
   d) collapsing the form and removing the form from the left ventricular device.

7. A method of maintaining the shape of a left ventricular assist device after forming the device and attaching one end of a vascular graft to the device, comprising:
   a) inserting an expandable and collapsible form into the left ventricular assist device, wherein said form comprises at least three evertable cones;
   b) expanding the form to fill space within the left ventricular assist device;
   c) allowing a period of time for healing of the left ventricular assist device; and
   d) collapsing the form and removing the form from the left ventricular device.

8. A method according to claim 7 wherein the evertable cones are provided with a flexible outer covering.

9. A method according to claim 8 wherein the flexible outer covering is porous PTFE.

10. A method of maintaining the shape of a left ventricular assist device after forming the device and attaching one end of a vascular graft to the device, comprising:
    a) using a collapsible form within the left ventricular assist device to fill space within the left ventricular assist device;
    b) allowing a period of time for healing of the left ventricular assist device; and
    c) collapsing the form and removing the form from the left ventricular device, wherein said form is collapsed by the sequential removal of individual segments.

11. A method of maintaining the shape of a left ventricular assist device after forming the device and attaching one end of a vascular graft to the device, comprising:
    a) using a collapsible form within the left ventricular assist device to fill space within the left ventricular assist device, wherein said form comprises a multiplicity of form segments which are individually removable;
    b) allowing a period of time for healing of the left ventricular assist device; and
    c) removing the multiplicity of form segments from the left ventricular device.

12. A method of maintaining the shape of a left ventricular assist device after forming the device and attaching one end of a vascular graft to the device, comprising:
    a) using a collapsible form within the left ventricular assist device to fill space within the left ventricular assist device, wherein said form comprises a length of material which is removable by the application of tension to an end of the length of material;
    b) allowing a period of time for healing of the left ventricular assist device; and
    c) removing the form from the left ventricular device.

13. A method according to claim 12 where the length of material is a length of tape.

14. A method according to claim 12 where the length of material is a length of cord.

15. A method according to claim 14 wherein the length of cord is contained in a flexible bag.

16. A method according to claim 15 wherein the bag is comprised of porous PTFE.

17. A method according to claim 12 wherein the length of material is a length of bead-chain contained in a flexible bag.

18. A method according to claim 17 wherein the flexible bag is comprised of porous PTFE.

* * * * *